(12) United States Patent
Matsumoto et al.

(10) Patent No.: US 6,501,829 B2
(45) Date of Patent: *Dec. 31, 2002

(54) GRID HOLDING FRAME, WHICH PROVIDES GRID INFORMATION TO X-RAY IMAGE PROCESSING APPARATUS

(75) Inventors: Kazuhiro Matsumoto, Utsunomiya (JP); Osamu Tsujii, Utsunomiya (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/392,617

(22) Filed: Sep. 9, 1999

(65) Prior Publication Data

US 2002/0015475 A1 Feb. 7, 2002

(30) Foreign Application Priority Data

Sep. 11, 1998 (JP) ............................................. 10-276484

(51) Int. Cl.[7] .................................................. G21K 1/00

(52) U.S. Cl. ........................ 378/154; 378/155; 378/164; 378/186

(58) Field of Search ............................ 378/7, 164, 181, 378/154, 155, 172, 174, 186, 114, 115, 116

(56) References Cited

U.S. PATENT DOCUMENTS 5,661,818 A * 8/1997 Gaborski et al. ............ 378/164
5,809,107 A * 9/1998 Schmitt ....................... 370/358

FOREIGN PATENT DOCUMENTS

JP 55-012429 1/1980
JP 56-11395 2/1981

* cited by examiner

Primary Examiner—Robert H. Kim
Assistant Examiner—Hoon K. Song
(74) Attorney, Agent, or Firm—Fitzpatrick, Cella, Harper & Scinto

(57) ABSTRACT

An X-ray image photographing apparatus includes an image obtaining portion for obtaining an X-ray distribution transmitted through an object, a grid detecting system having a construction for obtaining information from a grid side by the action of inserting the grid for decreasing scattered rays into the apparatus, and detecting at least one of the presence or absence of the grid, the kind of the grid and the presence or absence of the replacement of the grid by the use of the construction, an image processing system for image processing and outputting image data collected by the image obtaining portion, and a memory portion preserving therein a plurality of sets of image processing parameters for controlling the image processing system. The image processing system selects the image processing parameters preserved in the memory on the basis of at least the result of the detection by the grid detecting system and executes image processing.

21 Claims, 4 Drawing Sheets

GRID HOLDING FRAME, WHICH PROVIDES GRID INFORMATION TO X-RAY IMAGE PROCESSING APPARATUS

BACKGROUND OF THE INVENTION

1. Field of the Invention

This invention relates to an X-ray image photographing apparatus for effecting photographing by the use of a grid, and a grid device.

2. Related Background Art

When radiation such as X-ray, α-ray, β-ray, γ-ray, an electron beam, or an ultraviolet ray is applied to a ceratin kind of fluorescent material, part of this radiation energy is accumulated in the fluorescent material. It is known that excitation light such as visible light may be applied to this fluorescent material, whereby the fluorescent material exhibits accelerated light emission in conformity with the accumulated energy. The fluorescent material exhibiting such a nature is called an accumulative fluorescent material or an accelerative fluorescent material.

Heretofore, by the utilization of this accumulative fluorescent material, the radiation image information of an object such as a human body has been once recorded on a sheet of accumulative fluorescent material, and this sheet of accumulative fluorescent material has been scanned by the use of excitation light such as a laser beam to thereby emit accelerated light, and the obtained accelerated light has been read to thereby obtain an image signal. A radiation image information recording-reproducing system for outputting the radiation image of the object as a visible image to a recording material such as a photosensitive material or a display apparatus such as a CRT on the basis of this image signal is proposed, for example, by Japanese Patent Application Laid-Open No. 55-12429, Japanese Patent Application Laid-Open No. 56-11395, etc.

Also, in recent years, an apparatus using a semiconductor sensor to likewise photograph an X-ray image has been developed. These systems, as compared with a conventional radiation photographic system using silver salt photographs, have the practical advantage that an image can be recorded over a very wide range of radiation exposure area. That is, X-rays in a very wide dynamic range are read by photoelectric converting means and converted into an electrical signal. By the use of this electrical signal, the radiation image is outputted as a visible image to the recording material such as a photosensitive material or the display apparatus such as a CRT, whereby there can be obtained a radiation image which is not affected by the fluctuation of a radiation exposure amount.

However, in the analog photographing using the accumulative fluorescent material shown in the above-described example of the prior art, use is made of various grids for decreasing scattered rays during photographing, but in digital photographing using a semiconductor sensor, moire fringes are created from the relation between the sampling pitch and the frequency of the grid, and in an apparatus, a plurality of kinds of grids or an image by without a grid is not supported.

SUMMARY OF THE INVENTION

It is an object of the present invention to solve the above-noted problem and to provide an X-ray image photographing apparatus which can execute appropriate photographing or image processing by a plurality of kinds of grids or by without a grid and a grid device suitable therefor.

Other objects of the present invention will become apparent from the following description of an embodiment of the invention.

DESCRIPTION OF THE PREFERRED EMBODIMENTS

Figure 1:
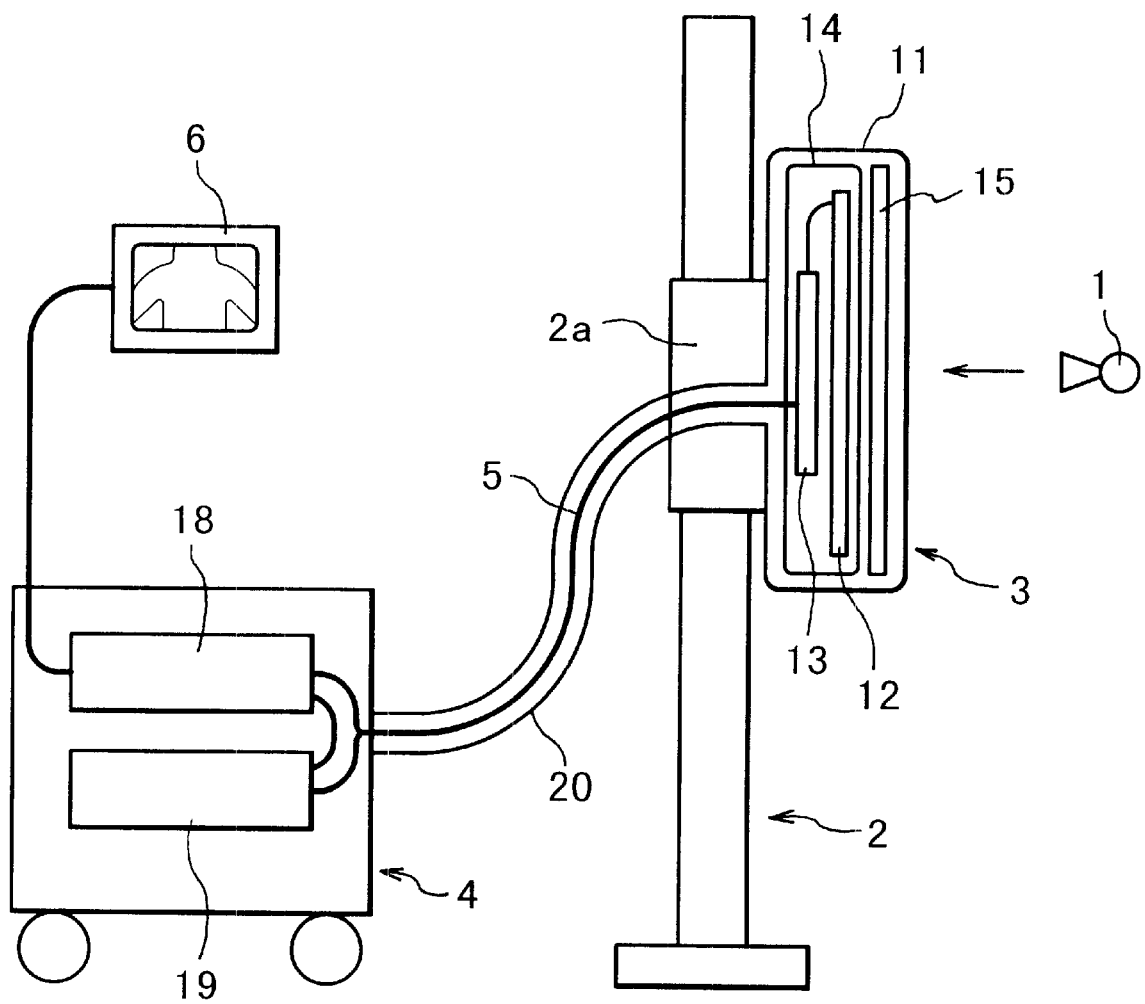
FIG. 1 is a schematic view of an embodiment of the present invention.

The present invention will hereinafter be described in detail with respect to an embodiment thereof shown in the drawings.

Figure 2:
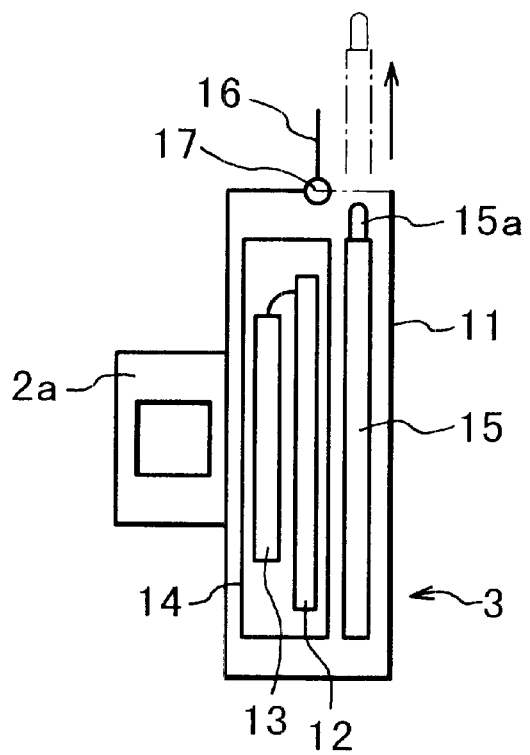
FIG. 2 is a plan view of an X-ray photographing portion.

FIG. 1 is a schematic view of an X-ray digital image photographing apparatus, and FIG. 2 is a plan view of the X-ray photographing apparatus. The X-ray digital image photographing apparatus is comprised of an X-ray generating portion 1 a stand 2, an X-ray photographing portion 3, a control portion 4 for controlling the X-ray photographing portion 3, a cable 5 for connecting the X-ray photographing portion 3 and the control portion 4 together, and a monitor 6 for displaying a signal processed in the control portion 4.

Also, the X-ray photographing portion 3 is vertically movable through the movable portion 2a of the stand 2, and can freely change its height in accordance with the position of an object by this vertical movement, and is designed to be capable of photographing the predetermined position of the object located between the X-ray photographing portion 3 and the X-ray generating portion 1.

An X-ray image receiving portion 14 comprising a radiation image detector 12 and a reading circuit 13 for reading out a signal from this radiation image detector 12, and a grid unit 15 including a grid for removing the scattered rays of the object are contained in the housing 11 of the X-ray photographing portion 3. Also, a handle 15a is provided on a side of the grid unit 15. Further, an openable-closable cover 16 is mounted on a side of the X-ray photographing portion 3 through a hinge 17.

The grid unit 15 and the X-ray image receiving portion 14 are disposed in parallel in the housing 11 of the X-ray photographing portion 3, and the grid unit 15 can be taken out of the X-ray photographing portion 3 by opening the cover 16 and pulling the handle 15a.

The control portion 4 is comprised of an image processing portion 18 for effecting a filtering process such as a reduction in the noise or edge emphasis of an image digital signal supplied from a memory circuit 13, and a power source portion 19 for supplying a power source to the X-ray image receiving portion 14 and the image processing portion 18. The connection between the X-ray photographing portion 3 and the control portion 4 is made by the cable 5 comprising a signal line and a power source line, and this cable 5 is covered and protected by a flexible tube 20. The flexible tube 20 is of a flexible material and therefore can follow the vertical movement of the X-ray photographing portion 3.

In an X-ray photographing apparatus system of such a construction, the X-ray photographing portion 3 is moved to a photographing position for a patient, and X-rays are applied from the X-ray generating portion 1 and photographing is effected. The image information of the object photographed by the X-ray photographing portion 3 is transmitted as a digital signal to the image processing portion 18 by the cable 5, and various image processings are effected in conformity with the presence or absence of the use and kind of the grid.

Figure 3:
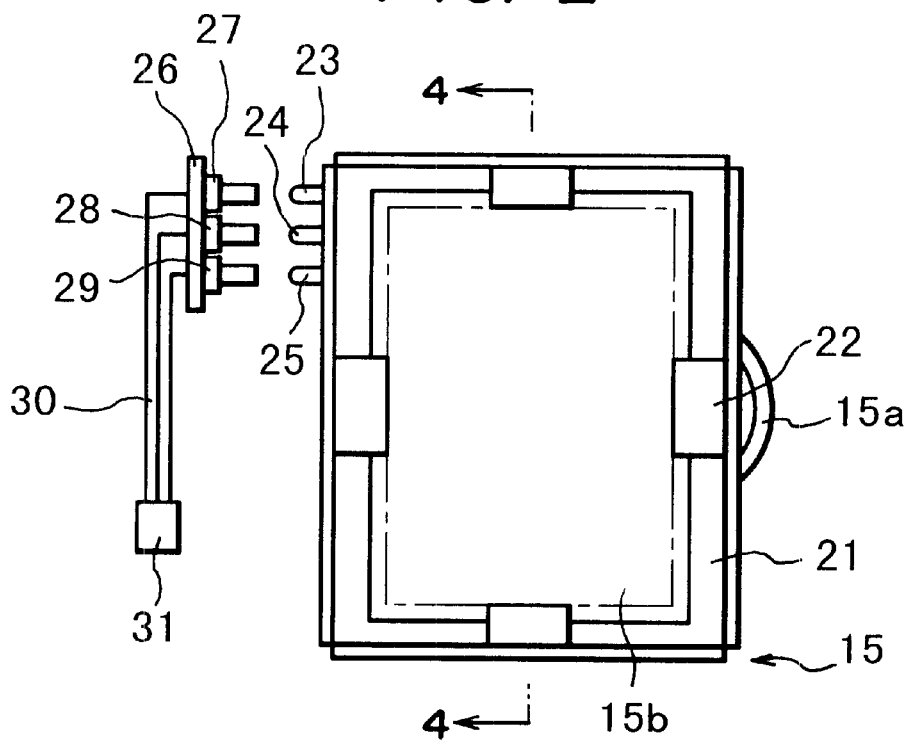
FIG. 3 is a front view of a grid.
Figure 4:
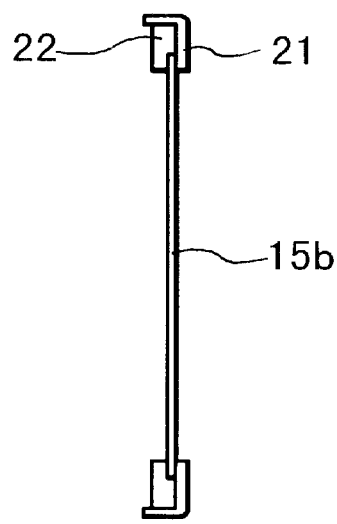
FIG. 4 is a cross-sectional view taken along the line 4—4 of FIG. 3.

FIG. 3 is a front view of a grid unit 15, and FIG. 4 is a cross-sectional view taken along the line 4—4 of FIG. 3. The grid unit 15 is comprised of a handle 15a, a grid body 15b and a grid holding portion 21, the grid body 15b mounted in the X-ray photographing portion 3 is fixed to the frame-like grid holding portion 21 through a fixing member 22, and the grid holding portion 21 has its four sides bent at right angles to improve the strength thereof. Of these four bent sides, convex projections 23, 24 and 25 are equidistantly formed on the end portion of the side of the surface opposed to the handle 15a. Also, a switch mounting plate 26 is provided in the X-ray photographing portion 3, and microswitches 27, 28 and 29 are provided on this switch mounting plate 26 so as to be opposed to the projections 23, 24 and 25, respectively, and a grid discriminating circuit 31 is connected to the microswitches 27, 28 and 29 through a lead wire 30.

The microswitch 27 is disposed so as to be changed from its OFF state to its ON state by the projection 23 provided on the grid holding portion 21 when the grid unit 15 is mounted on the X-ray photographing portion 3. Likewise, the microswitches 28 and 29 are adapted to be changed from their OFF state to their ON state by the projections 24 and 25, respectively. The ON and OFF states of the microswitches 27, 28 and 29 are transmitted to the grid discriminating circuit 31 by the lead wire 30, and the presence or absence of the grid body 15b and the kind of the grid body 15b are discriminated.

For example, it is conceivable to set so that if the microswitches 27, 28 and 29 are all in their ON state, it is discriminated that a grid body 15b of a first characteristic A is mounted, and if only the microswitch 27 is in its ON state, it is discriminated that a grid body 15b of a second characteristic B is mounted, and if all of the microswitches 27, 28 and 29 are in their OFF state, it is discriminated that the grid body 15b itself is not mounted.

Such setting is not restricted to this example, but various kinds of setting are possible depending on the combinations of the ON and OFF states of the microswitches 27, 28 and 29. The detecting means are nor restricted to the microswitches 27, 28 and 29, but may also be lead switches utilizing a magnetic force or photoswitches utilizing a light, and the number of the detecting means can be selected as required.

Further, while in the above-described embodiment, description has been made of a case where the stationary grid body 15b is used, such a detecting method is applicable not only to a photographing apparatus using the stationary grid 15b, but also to a photographing apparatus which effects photographing with the grid body 15b moved relative to the X-ray image receiving portion 14 during photographing. For example, driving means such as a motor for moving the grid body 15b may be discretely provided in the X-ray photographing portion 3, and the grid body 15b is made movable relative to the grid holding portion 21, and during photographing, only the grid body 15b can be moved at a predetermined speed by the driving means.

In this case, as in the above-described embodiment, the detected means provided on the grid holding portion 21 can be intactly used, and the presence or absence of the grid or the characteristic of the grid body 15b can be discriminated independently of the movement of the grid body 15b.

Such detecting means is not directly provided on the grid body 15b, but is provided on the common grid holding portion 21 to thereby obtain the following advantages. Irrespective of the grid thickness depending on the grid ratio, the grid inserting portion in the photographing apparatus can be simplified into the same shape, and in the case of photographing in which the grid is moved, the ON and OFF of the microswitches are not repeated each time the grid is moved and therefore, the durability of the apparatus is improved. Also, the grid can be protected when the grid is detached from the photographing apparatus. Further, if design is made such that the presence of the grid body 15b in the X-ray photographing portion 3 is detected and the grid driving means is operated only in the case of photographing in which the grid is moved, the grid driving means can be prevented from being driven by mistake when the grid body 15b is not mounted in the X-ray photographing portion 3 and when photographing is effected with the grid fixed.

Also, it will be unnecessary to provide new grid detecting means if design is made such that the grid detecting microswitches 27, 28 and 29 as described above are not used, but a parameter amount fluctuated by a load applied to the motor when only the grid driving means, e.g. the motor is operated before photographing, or during photographing is detected to thereby discriminate the presence or absence or the weight of the grid body 15b. Specifically, for example, the current value flowing to the motor when the motor is operated is defined as a parameter amount, and the current value when this current value has assumed a balanced state and a preset discrimination current value can be compared with each other to thereby discriminate the presence or absence of the grid body 15b and the characteristic of the grid body 15b which depends on the weight of the grid body 15b. Chiefly the amount of lead in the grid body 15b, i.e., the grid density, is conceivable as the characteristic of the grid body 15b which depends on the weight of the grid body 15b.

Figure 5:
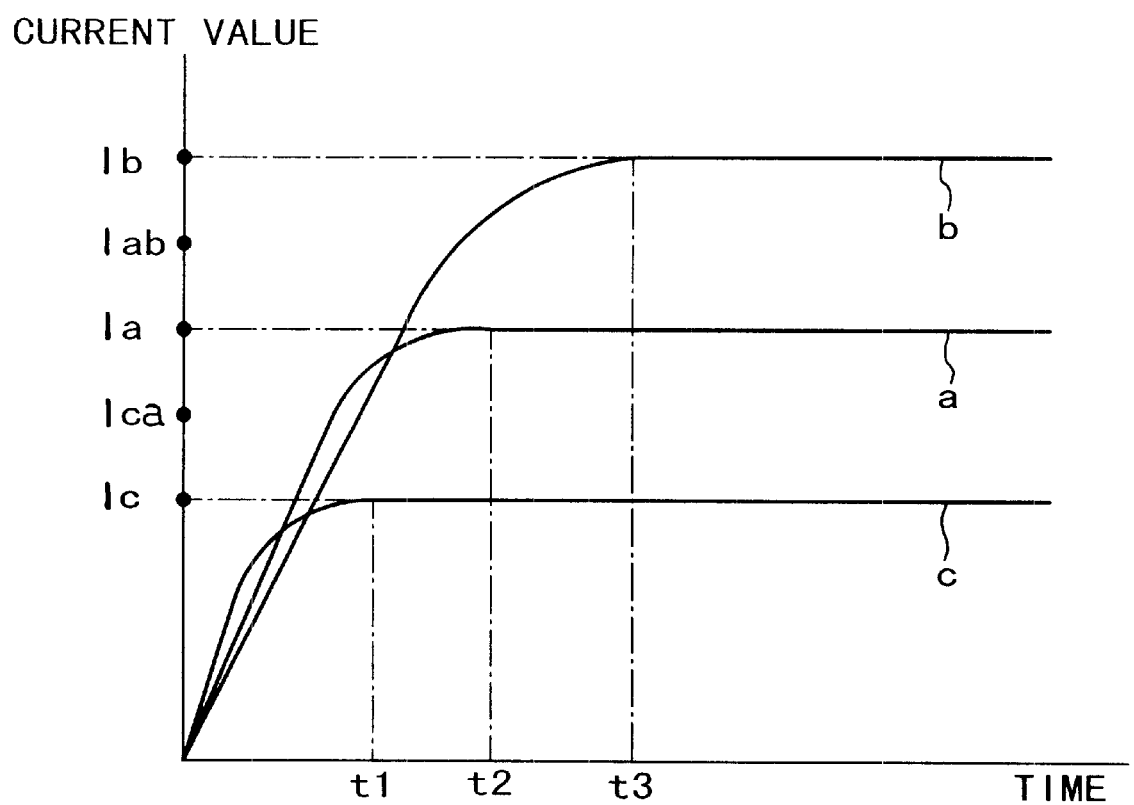
FIG. 5 is a graph of a current value flowing to a motor on the basis of a lapse time.

FIG. 5 is a graph showing the current value flowing to the motor to the lapse time. When the grid body 15b is not present in the X-ray photographing, portion 3, the load torque applied to the motor is minute and therefore, the current value from the start of the rotation of the motor changes as indicated by a curve C, and the current balance value converges to Ic after a current balance reaching time t1. Likewise, the current values when grids A and B are mounted become as indicated by curves a and b, respectively, and after current balance reaching times t2 and t3, the current values become Ia and Ib, respectively. The grid B is higher in grid density and greater in weight than the grid A and therefore, the load torque thereof becomes great, and the current values become Ib>Ia>Ic. Also, the increase rate of the current value during the rising of the rotation of the motor is great in the order of curves b, a and c, and the current balance reaching time becomes long in the order of t3>t2>t1.

Here, when discrimination current values Ica and Iab are preset so as to be Ib>Iab>Ia>Ic, it becomes known that if the current value i after the current balance reaching time t3 is Ica>i, no grid is mounted, and if Iab>i>Ica and i>Iab, the grids A and B are mounted respectively, and the discrimination of the presence or absence and the kind of the grid becomes possible. In the present embodiment, the parameter amount fluctuated by the load applied to the grid driving means is defined as the current value i in the balanced state, but may be defined as the increase rate of the current value or the required time until the balanced state is reached, and use may be made of the number of rotations of the motor inversely proportional to the load torque to obtain a similar effect.

Figure 6:
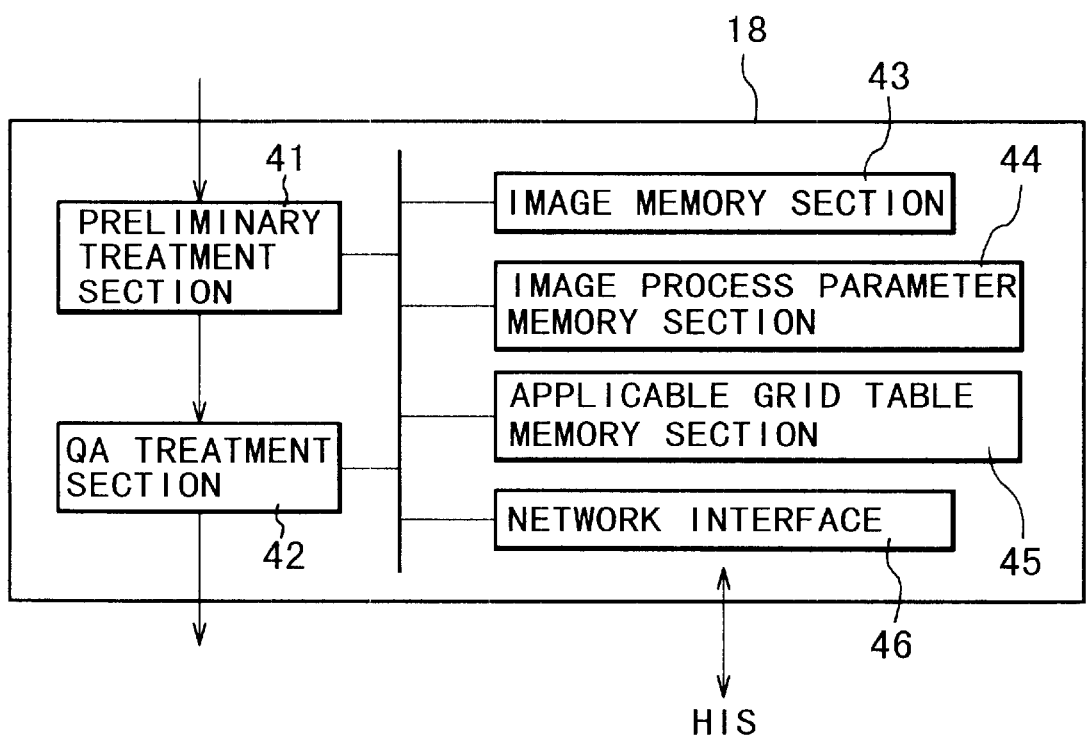
FIG. 6 is a block circuit diagram of an image processing portion.

FIG. 6 shows a block circuit diagram of the image processing portion 18, which can select appropriate image processing by the utilization of the information of the presence or absence and the kind of the grid body 15b obtained by the method as described above. The image processing portion 18 is comprised of a preliminary treatment section 41, a QA treatment section 42, an image memory section 43, an image process parameter memory section 44, an applicable grid table memory section 45 and a network interface 46. Gain correction, offset treatment, LOG conversion and grid erasing process, not shown, are carried out in the preliminary treatment section 41.

In the photographing in a fixed grid system, gain images are all photographed without the use of a grid. That is, in the fixed grid system, irrespectively of the presence or absence and the kind of the grid, the grid is not used but a photographed gain image W1 is used. Also, in the photographing in a movable grid system, gain images W2–W4 collected by the grid used in the photographing are used. One of the reasons for this is that energy characteristic differs from grid to grid and therefore gain images similar in the quality of lines to each other are used.

Again in the case of the movable grid system, when no grid is mounted, a gain image using no grid is used for correction. However, there is no possibility of shading occurring even if the gain image is not changed over by a grid and therefore, the quality of image will not be greatly affected even if the gain image is not changed over.

Such gain images W1–W4 are preserved in the image memory section 43, and by the control of the preliminary treatment section 41, an image process parameter table shown in Table 1 below which is preserved in the image process parameter memory section 44 is referred to from the result of the detection by the grid detecting means, and a corresponding gain image is down-loaded from the image memory section 43.

TABLE 1

| grid | gain image | grid erasing process | frequency emphasizing process | harmony processing |
| --- | --- | --- | --- | --- |
| no grid | W1 | absent | absent | gamma 4.4 |
| grid A | W2 | present, frequency Fa | present, frequency F1 | gamma 4.0 |
| grid B | W3 | present, frequency Fb | present, frequency F2 | gamma 4.0 |
| grid C | W4 | present, frequency Fc | present, frequency F3 | gamma 4.0 |

Likewise, the parameter of the grid erasing process is controlled by the presence or absence of the grid and the kind of the grid. The grid erasing process is carried out only in the case of the fixed grid system, and is not used in the case of the movable grid system. The advantage of the photographing by the fixed grid system is that high-speed photographing is possible, while on the other hand, the fringes of the grid are actualized in the image, and this is disliked as hindering diagnosis by some doctors. So, the erasing process of erasing the grid present in the image by image processing is carried out.

If the sampling frequency Fs of a sensor system is determined, in which frequency the fringes are created when which grid is used can be found by calculation. When the frequency of the grid is defined as Fg, if Fs>Fg, fringes are formed in the frequency Fg and therefore, they are removed by filter processing. As regards the frequency of the band cut filter at this time, the kind of the grid is detected, whereby the cut frequency Fa in the image process parameter table preserved in the image process parameter memory section 44 is determined.

Also, if Fs<Fg, the fringes of moire' are created in Fs−(Fg−Fs)=2Fs−Fg. As in this case, the frequency of this 2Fs−Fg is referred to from the image process parameter table by the band cut filter and a filter is constituted.

As regards also the frequency process which is one of QA processes, the parameter is adjusted by the grid. Here, the purposes are that in the grid processing, a frequency area weakened as a side effect is restored to its original state and that the grid which is not completely erased is not emphasized, but other frequency bands effective for diagnosis are emphasized. These filter parameters are also determined by searching for the image process parameter table on the basis of the grid information from the detecting means.

Finally, harmony processing is carried out, but generally in photographing which does not use a grid, although somewhat, the contrast of the entire image is reduced by scattered rays. In order to correct this, it is desirable to increase and convert the contrast in the harmony processing.

The process in which the parameter is changed depending on the presence or absence and the kind of the grid has been disclosed regarding the processing shown in Table 1, whereas the processing related to the grid is not restricted thereto, but also in image compression regarding the post-processing of a diagnosed image, it is conceivable for the parameter to be adjusted so as not to emphasized the grid. It is nor restricted to an adjusting method for the processed parameter utilizing grid information, but is determined by the desire of a doctor or an engineer.

In the foregoing, description has been made of the fact that the image processing parameter is adjusted by the information regarding the presence or absence or the kind of the grid, but changing the grid depending on the photographing method means that an appropriate grid is determined by the photographing method. In the image photographing apparatus of the present embodiment, before the photographing by the application of X-rays, the inputting of the photographing method as to what region is to be photographed with what intention is effected from a hospital information system HIS or a radiation information systems RIS by way of an input portion belonging to the display apparatus 17 or a network interface 46.

For example, suppose a case where if as shown in Table 2 below, the region to be photographed is the front of the breast, the use of the grid A is appropriate and if the region to be photographed is a limb, not using the grid is appropriate.

TABLE 2

| photographing method | grid |
| --- | --- |
| breast image | grid A |
| thoracic vertebrae image | grid B |
| limb image | no grid |
| head image | grid C |

In the present embodiment, the kind of an appropriate grid retrieved from the photographing method and the kind of the grid detected by the grid detecting means are compared with each other, and if the selected grid is not appropriate, the display apparatus 17 can be given the function of displaying it. The photographing method shown in Table 2 and the corresponding table of the grid are preset and can be preserved in the applicable grid table memory section 45.

While in the above description, it is premised to have the means for detecting the characteristic of the grid, and in FIG. 3, there are shown the construction of the grid unit 15 and a method of discriminating between the presence and absence of the grid in the photographing apparatus and a grid of what characteristic is mounted, the mechanism can also be simplified as a construction having only the means for detecting the presence or absence of the grid.

In this case, the determination as to a grid of what characteristic is mounted is effected by the use of discrete means. For example, there is adopted a construction in which the deviation of the present or absent state of the grid detected by grid presence or absence detecting means is monitored and whether the grid has been changed is detected by the presence or absence of a state in which the grid is absent, and when there is the replacement of the grid, a panel for requiring idle exposure for the selection of the kind of the grid is displayed on the display portion 12.

This idle exposure is photographed in a state in which there is no object and moreover, with the grid fixed. This fixed grid idle exposure image is analyzed by an image analyzing portion, not shown, provided discretely from the image processing portion 18, whereby the determination of the kind of the grid is effected. Frequency analysis using Fourier conversion can be used as the image analyzing method, and specifically, at the position of spectrum, it is possible to determine the grid ratio by the period of the grid and the size of the spectrum. After grid judgment has been done by the use of such an image analyzing method, the result of the determination is used for the selection of the image processing parameter as previously described.

As described above, the X-ray image photographing apparatus according to each of the above-described embodiments can detect the presence or absence, kind, etc. of the grid, and the execution of appropriate photographing or image processing becomes possible, and the grid device can be suitably utilized therefor.

What is claimed is:

1. An X-ray image photographing apparatus having:
   a photographing portion having an image obtaining portion for obtaining a distribution of X-ray having transmitted through an object, and can mount a grid unit including at least a grid for removing scattered rays from the object;
   a grid detection system for obtaining information from said grid unit or by using said grid unit, and detecting at least one of presence or absence of the grid, a kind of the grid and presence or absence of replacement of the grid; and
   a control portion for executing photographing or image processing on the basis of at least the result of the detection by said grid detection system.

2. The apparatus of claim 1, wherein said control portion having:
   an image-processing system for image-processing and outputting image data collected by said image obtaining portion; and
   a memory portion preserving therein parameters used in said image processing system;
   wherein said image processing system selects at least one of said parameters preserved in said memory portion on the basis of at least the result of the detection by said grid detection system and executes image processing.

3. The apparatus of claim 1, wherein further having:
   an image analyzing portion for effecting determination of a kind of the grid, on the basis of at least the result of the detection by said grid detection system, by analyzing image data obtained by said image obtaining portion with the grid fixed.

4. The apparatus of claim 1, wherein the detection by said grid detection system is effected when the grid unit is mounted on said photographing portion.

5. The apparatus of claim 1, wherein said image obtaining portion has a semiconductor sensor.

6. The apparatus of claim 1, wherein said image obtaining portion has a fluorescent material sheet.

7. The apparatus of claim 1, wherein said grid detection system has a switch member which effects switching corresponding to a shape of a predetermined region of said grid unit, and at least one of presence or absence of said grid, a kind of the grid and presence or absence of replacement of the grid is detected by the switching of said switch member.

8. The apparatus of claim 1, further having:
   an inputting portion by which photographing information as to which portion of the object is photographed is input;
   wherein said control portion having a judging portion for judging the propriety of the adaptation of the grid on the basis of at least the photographing information input by said inputting portion and the result of the detection by said grid detection system.

9. The apparatus of claim 8, wherein said control portion further having a grid memory portion preserving therein information of an applicable grid corresponding to the photographing information.

10. The apparatus of claim 8, further having a display portion for displaying the result of the judgment of said judging portion.

11. An X-ray image photographing apparatus having:
    sensor means for obtaining a distribution of X-ray having transmitted through an object;
    housing means for housing said sensor means, and can mount a grid unit including at least a grid for removing scattered rays from the object;
    grid detecting means for obtaining information from said grid unit or by using said grid unit to thereby detect at least one of presence or absence of the grid, a kind of the grid and presence or absence of replacement of the grid; and
    control means for executing photographing or image processing on the basis of at least the result of the detection by said grid detection means.

12. The apparatus of claim 11, wherein said control means having:
    image processing means for determining an image processing parameter on the basis of at least the result of the detection by said grid detection means for image data collected by said sensor means and executing image processing.

13. The apparatus of claim 11, wherein further having:
    image analyzing means for effecting determination of a kind of the grid, on the basis of at least the result of the detection by said grid detection means, by analyzing image data obtained by said sensor means with the grid fixed.

14. The apparatus of claim 11, wherein the detection by said grid detection means is effected when the grid unit is mounted on said housing means.

15. The apparatus of claim 11, wherein said grid detection means having switch means which effects switching correspondingly to a shape of a predetermined region of said grid unit, and at least one of presence or absence of the grid, a kind of the grid and presence or absence of replacement of the grid is detected by the switching of said switch means.

16. The apparatus of claim 11, further having:
   input means for inputting photographing information as to which portion of the object is photographed;
   wherein said control means having judging means for judging the propriety of the adaptation of the grid on the basis of at least the photographing information input by said input means and the result of the detection by said grid detection means.

17. The apparatus of claim 16, further having display means for displaying the result of the judgment of said judging means.

18. A grid device for use in an X-ray image photographing apparatus having:
   a grid;
   a frame holding said grid; and
   information providing means provided on said frame, said information providing means being designed to provide information concerning at least one of presence or absence of the grid, a kind of the grid and presence or absence of replacement of the grid to said X-ray image photographing apparatus.

19. The device of claim 18, wherein said information providing means has a projection for operating a micro switch provided on said X-ray image photographing apparatus.

20. The device of claim 18, wherein said grid is made movable relative to said frame.

21. An X-ray image photographing apparatus having:
   a photographing portion having an image obtaining portion for obtaining a distribution of X-ray having transmitted through an object, and can mount a grid unit including at least a grid for removing scattered rays from the object;
   a grid detection system detecting at least one of presence or absence of the grid, a kind of the grid and presence or absence of replacement of the grid; and
   an image processing system for determining an image processing parameter concerning at least one of gain correction, frequency processing, contrast processing and image compression on the basis of at least the result of the detection by said grid detection system for image data obtained by said image obtaining portion and executing image processing.

\* \* \* \* \*

UNITED STATES PATENT AND TRADEMARK OFFICE
CERTIFICATE OF CORRECTION

PATENT NO. : 6,501,829 B2
DATED : December 31, 2002
INVENTOR(S) : Kazuhiro Matsumoto et al.

It is certified that error appears in the above-identified patent and that said Letters Patent is hereby corrected as shown below:

Column 1,
Line 13, "ceratin" should read -- certain --.
Lines 58 and 67, "by" should be deleted.

Column 2,
Line 27, "portion 1" should read -- portion 1, --.

Column 3,
Line 36, "set" should read -- set the microswitches --.
Line 47, "nor" should read -- not --.

Column 4,
Line 41, "to the lapse" should read -- versus the lapsed --.
Line 42, "photographing," should read -- photographing --.

Column 6,
Line 34, "nor" should read -- not --.

Column 7,
Line 47, "can mount" should read -- capable of mounting --.
Line 60, "having:" should read -- has: --.
Line 65, "system;" should read -- system, --.

Column 8
Lines 3 and 59, "wherein" should be deleted.
Line 24, "input;" should read -- input, --.
Lines 25 and 31, "having" should read -- has --.
Line 40, "can" should be deleted.
Line 41, "mount" should read -- capable of mounting --.
Line 53, "having:" should read -- has: --.
Lines 56 and 57, "means" should read -- means, --.

UNITED STATES PATENT AND TRADEMARK OFFICE
CERTIFICATE OF CORRECTION

PATENT NO. : 6,501,829 B2
DATED : December 31, 2002
INVENTOR(S) : Kazuhiro Matsumoto et al.

It is certified that error appears in the above-identified patent and that said Letters Patent is hereby corrected as shown below:

Column 9,
Lines 2 and 10, "having" should read -- has --.
Line 9, "photographed;" should read -- photographed, --.

Column 10,
Line 5, "on" should read -- in --.
Line 12, "can mount" should read -- capable of mounting --.
Line 22, "system" should read -- system, --.
Line 23, "portion" should read -- portion, --.

Signed and Sealed this

Eighteenth Day of November, 2003

JAMES E. ROGAN
*Director of the United States Patent and Trademark Office*